United States Patent [19]

Whiteside

[11] 4,439,315

[45] Mar. 27, 1984

[54] METHANE GENERATOR

[76] Inventor: C. H. Whiteside, 2600 Dudley Rd., Kilgore, Tex. 75662

[21] Appl. No.: 386,226

[22] Filed: Jun. 8, 1982

[51] Int. Cl.³ .............................................. C02F 11/04
[52] U.S. Cl. ..................................... 210/90; 210/91; 210/120; 210/151; 210/926; 435/167; 48/197 A
[58] Field of Search ............... 210/603, 602, 218, 614, 210/86, 90, 91, 120, 610, 611, 617, 926, 150, 151, 188; 48/197 A; 47/58; 435/167, 316

[56] References Cited

U.S. PATENT DOCUMENTS

| | | |
|---|---|---|
| 3,572,506 | 3/1971 | Bandy, Jr. et al. .................. 210/120 |
| 3,933,628 | 1/1976 | Varani ................................ 210/603 |
| 4,169,050 | 9/1979 | Serfling et al. ..................... 210/602 |
| 4,198,211 | 4/1980 | Shattock ............................ 210/603 |
| 4,316,961 | 2/1982 | Klass et al. ......................... 210/602 |
| 4,329,428 | 5/1982 | Ghosh et al. ....................... 210/603 |

FOREIGN PATENT DOCUMENTS 1032721 6/1978 Canada ................................ 210/120

OTHER PUBLICATIONS

McDonald, R. C. et al., "Treating Domestic Wastewater with Water Hyacinths", NASA Tech. Briefs, (Fall 1980), p. 336.

Primary Examiner—Benoît Castel
Attorney, Agent, or Firm—B. Kreten

[57] ABSTRACT

A biogas generator which includes a medium conducive to the growing of plants that are floating and of the family that includes water hyacinths, lily pads, and elodea; a conveyor for transferring the free floating plants from the growing area to a decomposition area including a canopy adapted to entrain therewithin biogas given off by decomposing plants constrained thereunder, and an instrumentality for scavenging the biogas generated therein to a remote area for subsequent use and or compression.

10 Claims, 5 Drawing Figures

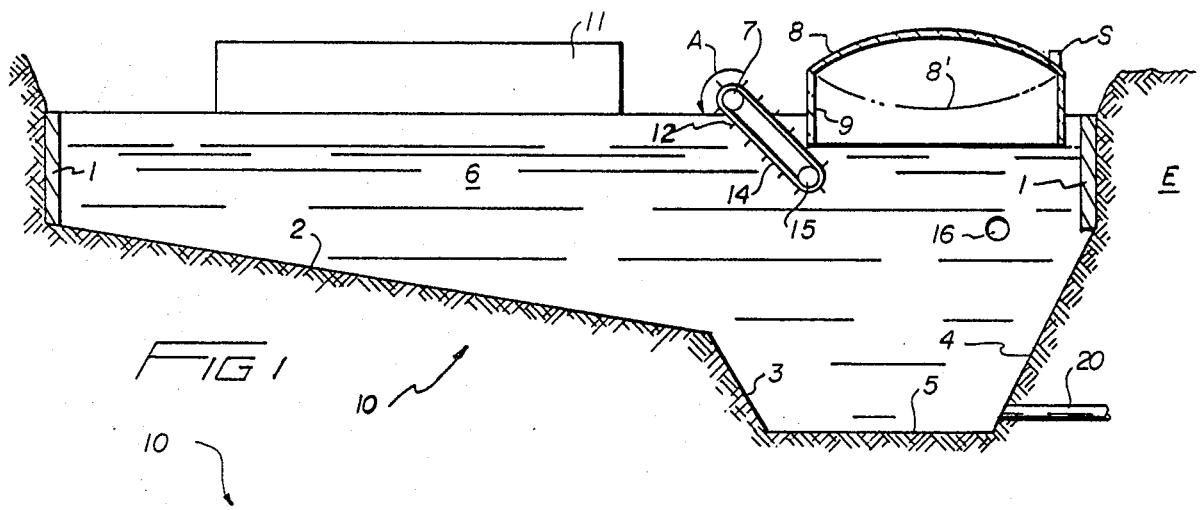
FIG 1
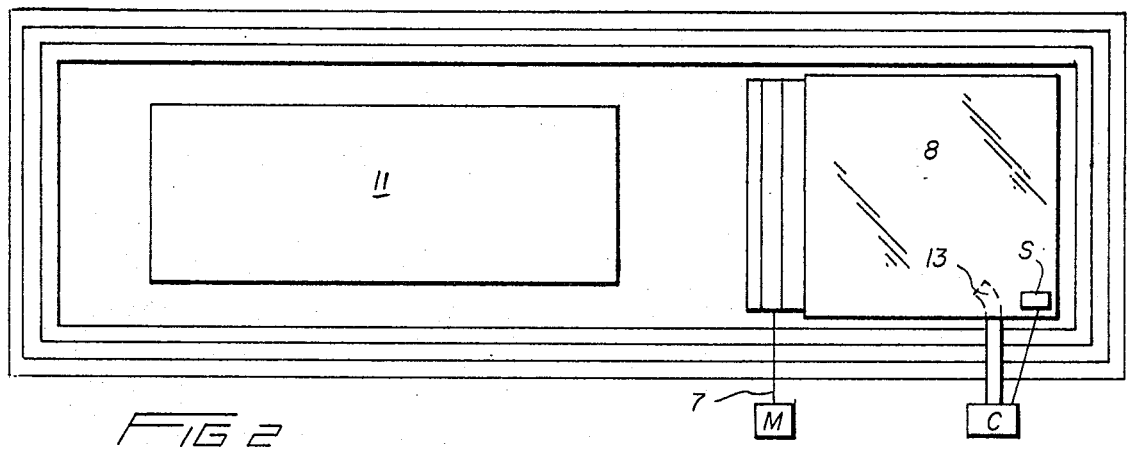
FIG 2
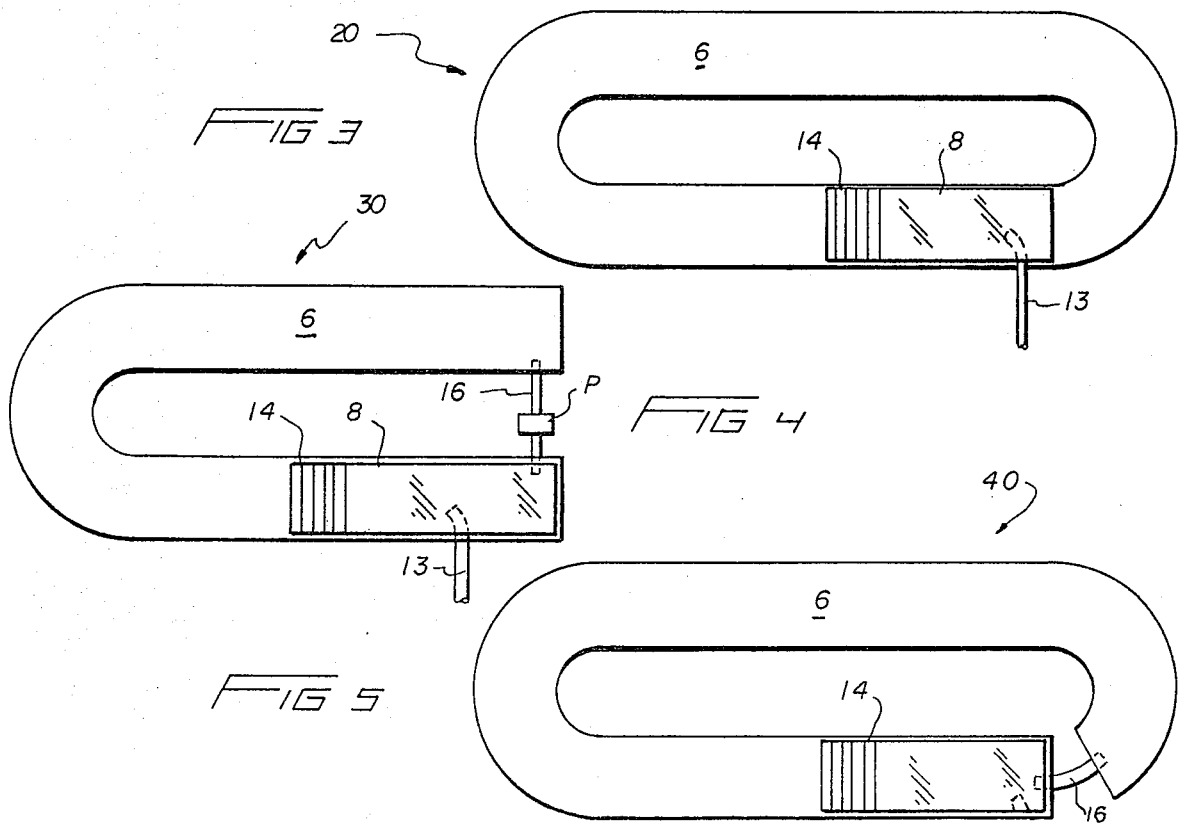
FIG 3
FIG 4
FIG 5

METHANE GENERATOR

BACKGROUND OF THE INVENTION

The following invention relates generally to generators for producing methane from organic matter commonly referred to as biogas.

As is generally known, decomposition of organic matter generally has associated therewith the liberation of certain fermentation by-products which heretofore have not been harnessed for any usful purpose and therefore allowed to escape.

While perhaps at one time such handling was not considered extravagant, the steadily increasing cost associated with energy has resulted in a crying need for devices similar to that which is disclosed herein so as to efficiently harness resources that are readily available, but heretofore not utilized.

The following patents reflect the state of the art of which applicant is aware, insofar as they appear to be germane to the patent process:

U.S. Pat. No. 1,919,689: Elrod
U.S. Pat. No. 3,812,620: Titus et al.
U.S. Pat. No. 3,981,803: Coulthard
U.S. Pat. No. 4,100,023: McDonald
U.S. Pat. No. 4,157,958: Chow McDonald teaches the use of a known prior art methane generator wherein plural slurry chambers are interconnected by pass-through tubes for sequential advancement of organic matter. An exemplary chamber includes a digester bag 30 for retaining biogas and an evacuation system for extracting gas therefrom for subsequent compression.

The remaining citations show the state of the art further.

By way of contrast, the invention as defined in the instant application is directed to and claims a biogas generator that provides a plant growing medium disposed in an instrumentality and having a plurality of plants therein, an area suitably formed to allow the decomposition of the plants, which upon said decomposition produces the desired gas, an instrumentality for conveying the plants into the gas generating decomposition area and an instrumentality for collecting the gas exuded therefrom defining a further reservoir and an instrumentality for ultimately transferring the biogas from an area remote from the reservoir.

SUMMARY AND OBJECTS OF THE INVENTION

Accordingly, this invention has an objective the provision of a novel biogas generator which can continuously provide the beneficial methane associated therewith.

It is still a further object of this invention to provide a device of the character described above which is extremely inexpensive to use when once constructed.

It is a further object of this invention to provide a device of the character described above which is relatively inexpensive to install.

It is a further object of this invention to provide a device of the character described above which is durable in construction and requires minimal maintenance.

It is still yet a further object of this invention to provide a device in accordance with the objectives set out hereinbefore in which the rate of methane production can be reliably controlled.

These and other objects will be made manifest when considering the following detailed specification when taken in conjunction with the appended drawing figures.

BRIEF DESCRIPTION OF THE DRAWING FIGURES

FIG. 1 is a sectional view of the apparatus in one preferred form.

FIG. 2 is a top plan view of that which is shown in FIG. 1.

FIG. 3 is a schematic depiction of another embodiment.

FIG. 4 denotes yet another embodiment.

FIG. 5 shows still a further depiction of a possible arrangement of components associated with the instant invention.

BRIEF DESCRIPTION OF THE PREFERRED EMBODIMENT

Referring to the drawings now, wherein like reference numerals refer to like parts throughout the various drawing figures, reference numeral 10 is directed to the embodiment for a methane generator according to one form of the invention.

As depicted in FIGS. 1 and 2, the device includes a fluid reservoir having liquid 6 contained therein, the liquid in the preferred form being water having sufficient nutrients to sustain life of plants that can generally be described as aquatic, taken from the groups included water hyacinth, lily pads, or elodea.

The reservoir includes a vertical wall 1, a horizontal floor portion 5 preferably of greatest depth, sloped walls 3 and 4 extending away from the vertical floor, and a further angled wall 2 communicating portions of the vertical wall 1 with the angled wall 3.

In a further preferred form of the invention, a cover 11 is optionally provided to allow the free floating plants described above to grow in more extreme temperature climates than would be possible without the cover 11, to create a "greenhouse effect", and therefore the cover 11 is preferably light transmissive. A further cover 8 is provided which is opaque, and through which radiation that is beneficial to the plants does not pass such that plants contained within this opaque covering 8 tend to decompose. In order to assist in the migration of plants from the areas without the opaque covering 8 therewithin, a conveyor 14 is provided having an upper shaft 7 and a lower shaft 15 at opposed extremities of the conveyor belt 14, and a motor M is operatively attached to the roller shaft 7 forming one of the shafts, so that the motor will cause appropriate rotation of the belt 14 in the direction of the arrows A so as to encourage the free floating plants to be disposed within the opaque covering 8.

The covering 8 includes a vertical side wall portion 9 suitably formed to be partially submerged within the water, the top most portion of the opaque covering 8 being substantially flexible so as to gravitate between a first position 8' and a second position shown as reference numeral 8, the second position indicative of the presence of gas within the enclosure defined by the portions 8 and 9. Mounted on one of the vertical walls 9, a switch S is provided which is used to sense the presence of the flexible covering 8' from its lowermost position to its uppermost, whereupon a scavenging pipe 13 is provided in operative communication with a topmost portion of the opaque covering so as to scavenge the gas which is collected therewithin, the scavenging pipe 13 communicating with a compressor C operatively conditioned by the switch S when necessary so that the gas may be thereafter optionally removed of water and more efficiently stored. The covering 11 which allows plants to grow during an extended or greater growing time, is preferably of light transmissive clear material, commonly found in use in the greenhouse environment.

FIGS. 1 and 2 are directed to a substantially rectangular type of reservoir for conditioning the plants set forth above so that once under the cover 8, a decomposition of the plants provides methane gases. FIGS. 3 through 5 provide means by which similar floating plants can be harnessed and FIG. 3 is directed to a substantially oval or racetrack shaped configuration, in which the liquid 6 is disposed in a closed loop. FIG. 4 teaches the use of a reservoir in which the opposed free ends of a U-shaped reservoir are allowed to communicate by means of a further conduit 16 (also shown in FIG. 5) which in this form, has a pump P interposed therebetween so that while there is a general tendency of the liquid contained within the reservoir to achieve one uniform level, a circulatory effect can be made by causing the pump P to have water migrate from one to the other free end of the U-shaped reservoir so as to assist in the circulation and flow of the liquid.

Finally, FIG. 5 teaches the use of a further form of the invention 40 in which the oval has an interrupted portion, and a berm E is provided traversed by the pipe 16 as shown which may or may not have the optional pump P for the attendent benefits set forth hereinabove.

Having thus described the invention, it should be apparent that in use and operation, plural ponds having diverse shapes are provided, the pond is filled with water and plants. Nutrients are added for the growth of the aquatic plants. One portion of the pond is covered with an opaque gas tight floating cover while the other portion of the pond allows for the growth of the material. By means of the conveyor belt 14, suitably equipped with paddles 12, aquatic plants are conveyed under the cover, where they die from lack of light and begin to ferment so as to produce biogas which is 60-70 percent methane. While the conveyor is shown as being mechanically powered, on small systems it can be hand powered. The amount of plant material conveyed under the cover will determine the rate of gas production. Thereafter, the hose or pipe 13 causes biogas to be drawn therewithout which may subsequentially be compressed in a tank or have suitable operations performed thereon for removal of associated water therewithin. The switch S is operatively conditioned to the cover so that when the cover is expanded and therefore indicative of a situation in which a sufficient quantum of biogas is present, the compressor is actuated to remove the biogas therefrom for subsequent conditioning. Sufficient gas removal of course causes the cover to drop which deactivates the switch and turns the compressor off. Compressed gas may be returned to the lower fermentation area 20 and allowed to bubble up from the bottom as a means of mixing and stirring the fermenting plants. Such mixing and stirring could accelerate the fermentation process. When an oval shaped pond is used, a small unexcavated area or berm provided with a pipe is used to regulate the flow of water from the digester (at a perferred intermediate depth), the purpose being to prevent floating plants from passing out of the digester area. Since only the conveyor 14 is used to push the plants within the digester area, to augment the water flow, a pump may be associated with the berm pipe 16 so as to encourage a more uniform circulation when the U-shaped or other pond is provided since it may not get the total effect of the circulation through the means of the conveyor alone. While the device includes a growing area 11 for extending the traditional growing season, benefiting from a greenhouse effect, it is also possible that a plurality of plants could be grown so that the plants even though frost bitten can be fermented during the winter months and the fermentation process will serve to assist in keeping the growing area essentially warm so that biogas and therefore methane production can be continue year around.

Having thus described the invention, it should be apparent that numerous structural modifications are contemplated as being a part of this invention as set forth hereinabove and as defined hereinbelow by the claims.

What is claimed is:

1. A biogas generator comprising, in combination:
   a liquid reservoir having first and second distinct zones and
   a liquid which supports plant growth in said reservoir and therefore said zones,
   a first said zone of said reservoir growing a supply of plant biomass therein,
   a second said zone of said reservoir contiguous with said first zone to receive and biodegrade said plant biomass producing a biogas,
   collection means including an imperforate opaque top wall to encourage plant decomposition overlying said second zone to collect said biogas produced therein,
   conveying means at a boundary of said zones to convey said plant biomass from said first zone to said second zone as needed to control the amount of biogas produced,
   and scavenging means to draw off biogas from said collection means to a site of storage and use
   whereby said plant biomass is continuously harvestable and biodegraded to produce a biogas to be used as an energy source and said plant biomass once degraded serves as nutrient for further plant biomass growth defining a continous closed system.

2. The device of claim 1 wherein said biogas collection means includes perimeter side walls of substantially rigid configuration, and a flexible, top wall sealingly disposed on top of said perimeter walls, whereby said flexible top wall is adapted to deform from a first unstressed position to a second stressed position indicative of the presence of gas therebelow.

3. The device of claim 2 wherein switching means are disposed upon said biogas collection means adapted to condition a compressor means associated with scavenging means for removing biogas below said top wall upon energization of said switch means.

4. The device of claim 3 wherein said scavenging means includes a conduit communicating said compressor means with said perimeter wall to assist in the scavenging of biogas from an area disposed below said flexible top wall and above the liquid within said reservoir.

5. The device of claim 4 wherein said conveying means includes a conveyor having an endless belt and associated supporting axles at extremities thereof, including an upper and lower extremity, said upper extremity powered by a motor means for operative manipulation of said belt.

6. The device of claim 5 wherein said conveyor means includes a plurality of laterally outwardly extending paddles emanating from said belt to engage said plant biomass and causes same to be inducted into said second zone.

7. The device of claim 6 wherein said reservoir further includes a conduit extending between remote extremities thereof to allow communication and circulation of said fluid between the extremities.

8. The device of claim 7 wherein said conduit is enabled by a pumping means.

9. The device of claim 8 wherein said first zone includes a light transmissive greenhouse canopy to enhance growth.

10. The device of claim 9 further including
a further conduit communicating between said scavenging means and a lowermost portion of said second zone to disperse biogas thereat so as to circulate said plant biomass and enhance its decomposition, and
said collection means is buoyant to float above said second zone.

* * * * *